(12) United States Patent
Tapson et al.

(10) Patent No.: US 8,838,219 B2
(45) Date of Patent: Sep. 16, 2014

(54) PREGNANCY TEST SYSTEM

(75) Inventors: Jonathan Craig Tapson, Epping (AU);
Gaetano Gargiulo, Monterey (AU);
Richard William Shepard, Maffra (AU)

(73) Assignee: Heard Systems Pty Ltd, New South Wales (AU)

( * ) Notice: Subject to any disclaimer, the term of this patent is extended or adjusted under 35 U.S.C. 154(b) by 0 days.

(21) Appl. No.: 13/816,908

(22) PCT Filed: Aug. 12, 2011

(86) PCT No.: PCT/AU2011/001033
§ 371 (c)(1),
(2), (4) Date: Apr. 19, 2013

(87) PCT Pub. No.: WO2012/019242
PCT Pub. Date: Feb. 16, 2012

(65) Prior Publication Data
US 2013/0204148 A1   Aug. 8, 2013

(30) Foreign Application Priority Data
Aug. 13, 2010  (AU) ............................... 2010903650

(51) Int. Cl.
*A61B 5/04* (2006.01)
*A61B 7/04* (2006.01)
*A61D 17/00* (2006.01)
*A61B 5/0408* (2006.01)
*A01K 29/00* (2006.01)

(52) U.S. Cl.
CPC ................ *A61D 17/006* (2013.01); *A61B 7/04* (2013.01); *A61B 5/0408* (2013.01); *A01K 29/005* (2013.01)

USPC .......................................................... 600/509

(58) Field of Classification Search
CPC ... A61B 5/0452; A61B 5/0006; A61B 5/0428
USPC .......................................................... 600/509
See application file for complete search history.

(56) References Cited

U.S. PATENT DOCUMENTS

| | | |
|---|---|---|
| 5,471,993 A | 12/1995 | Yoches et al. |
| 5,542,431 A | 8/1996 | Starzl et al. |
| 6,491,647 B1 * | 12/2002 | Bridger et al. ............... 600/585 |
| 2011/0190581 A1 * | 8/2011 | Bennett et al. ............... 600/109 |

FOREIGN PATENT DOCUMENTS

WO   WO 2010/055011 A1   5/2010

OTHER PUBLICATIONS

International Search Report, dated Dec. 6, 2011, corresponding to PCT/AU2011/001033, 2 pages.

\* cited by examiner

*Primary Examiner* — George Manuel
(74) *Attorney, Agent, or Firm* — Christie, Parker & Hale, LLP

(57) ABSTRACT

A pregnancy test system (10) includes a carrier (14) carrying a plurality of (sensors 12) arranged in a fixed relationship relative to one another. A signal processing (circuit 42) processes data sensed by the sensors (12) and outputs a data signal representative of the pregnancy status of an animal being examined. A support arrangement (24) supports the carrier (14) in a desired position relative to the animal. A positioning mechanism (26) is associated with the carrier (14) for positioning the carrier (14) at the desired position relative to the animal.

17 Claims, 6 Drawing Sheets

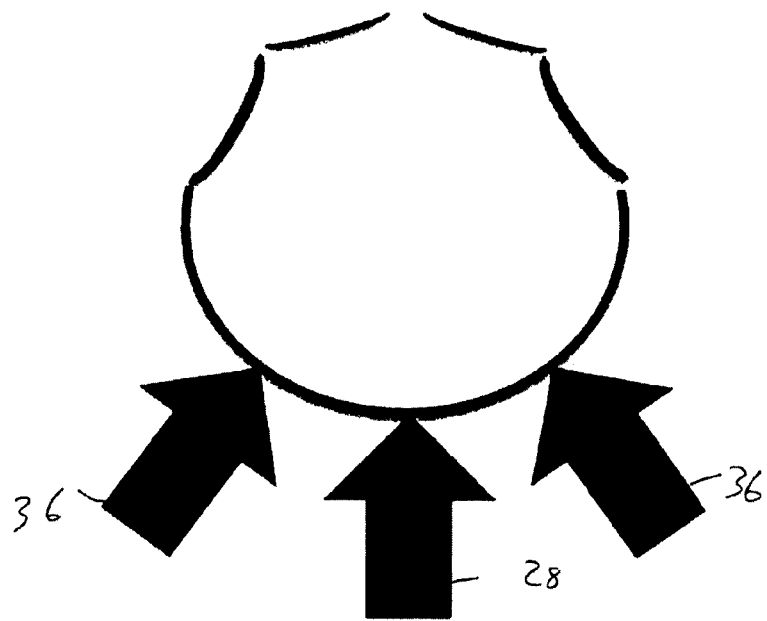
Fig. 5
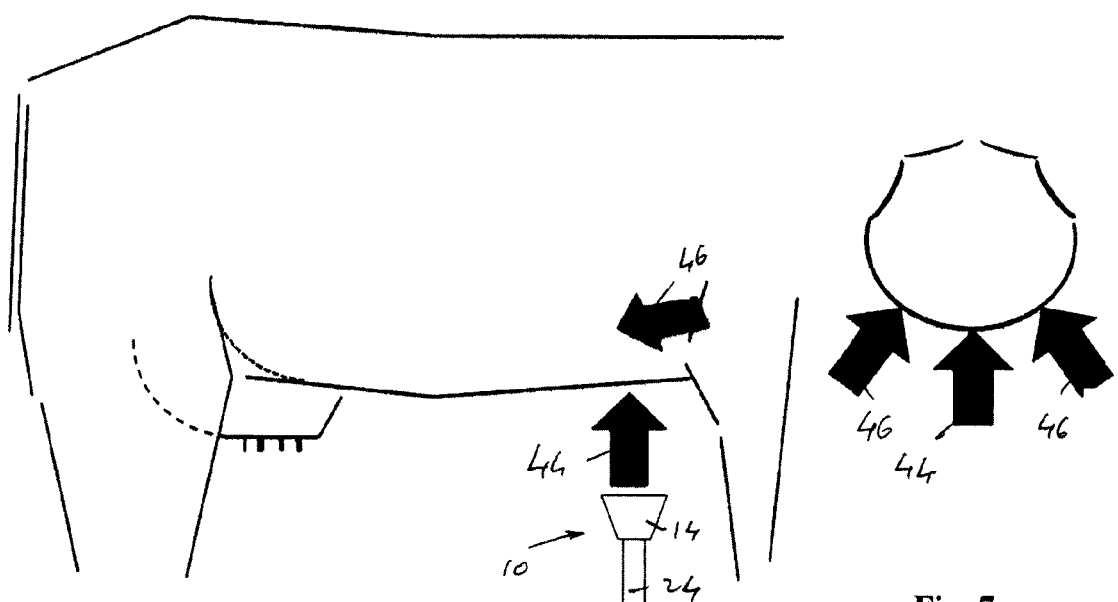
Fig. 6
Fig. 7

PREGNANCY TEST SYSTEM

CROSS-REFERENCE TO RELATED APPLICATIONS

This application is a national phase application under 35 U.S.C. §371 of International Application No. PCT/AU2011/001033 filed on Aug. 12, 2011 which claims the benefit of Australian provisional patent application no. 2010903650 dated Aug. 13, 2010, the contents of both of which are incorporated herein by reference in their entirety.

FIELD

This disclosure relates, generally, to a pregnancy test system and, more particularly, to a pregnancy test system suitable for use on animal handling systems such as, for example, animal milking machines. The system can also be used to monitor existing pregnancies, assess the health of the animal under examination and to detect non-pregnant animals.

BACKGROUND

Detecting pregnancy in large agricultural animals (such as cows) is one of the most frequently performed diagnostic procedures. Timely testing of individual animals for pregnancy supports optimal management of individual animals and the maximization of farm profit for both the dairy and beef production systems.

The two most frequently used methods for pregnancy diagnosis of cattle are manual palpation of the reproductive tract (per rectum) and transrectal ultrasonography of the reproductive tract. Veterinarians and specialist animal technicians most commonly provide these services to farmers. Both procedures are invasive and practitioners require extensive training in order to undertake the procedure safely (for cow and operator).

Automated milking systems represent a completely new way of handling agricultural animals, which is likely to become more widespread, particularly in countries with high labour costs or shrinking rural labour pools. In automatic milking systems (AMS), cows are trained to circulate voluntarily through the milking system while en route from one feeding location to another. While in the milking system, milking cups are attached robotically to the cow's teats and the cow stands at rest until milking is finished—a process which takes a few minutes. This time while the animal is at rest represents an ideal time to undertake a pregnancy test on the animal.

AMS systems are most cost-effective when the usage is spread evenly over a full 24 hour period, so they require a change from batch processing of a whole herd of cows twice a day to individual processing spread over the full 24 hours. Two consequences are that, firstly, it becomes counterproductive to batch the cattle together for any reason as this upsets their training (and very often the farm is no longer optimised in either physical layout or labour availability to support herding together of cattle); and, secondly, the management process becomes dependent on individual animal data from the AMS, such as animal weight, milk production and quality, and in some cases state of oestrus (inferred by reading an animal-mounted electronic pedometer while the animal is in the AMS). It therefore would be useful and sensible to be able to test for pregnancy as part of the AMS process so that the cows are not unsettled by the batching and physical discomfort of conventional testing, and so that the data is available to be integrated with the other information used by the farm manager.

Similar developments are occurring in other animal industries and include automated gating and access points operated by individual animal RFID tags, virtual fencing and automatic drafting systems. Most are characterised by isolation of an individual animal from the group (usually via voluntary entry through a gate), identification of the animal by reading an RFID ear tag or similar and controlled and directed release. Systems that use these principles are suitable for the inclusion of an automated pregnancy testing system.

There are also many circumstances where non-dairy animals are handled using fixed-in-place machinery, such as conventional animal handling restraint systems, known in the industry as crushes or chutes and also in systems which apply restraint to the animal whilst feeding, for example, in the form of restraining head-stalls. Other examples are milking parlour bales and voluntary entry systems such as automated feeding stations. All the above systems serve to restrain the animal in some fashion and provide a suitable opportunity to conduct a pregnancy test on the animal.

SUMMARY

In a first aspect there is provided a pregnancy test system which includes
  a carrier carrying a plurality of sensors arranged in a fixed relationship relative to one another;
  a signal processing circuit for processing data sensed by the sensors and for outputting a data signal representative of the pregnancy status of an animal being examined, the signal processing circuit being operative to minimise artifacts to enable at least one signal of interest to be analysed in the signal processing circuitry using a plurality of techniques in parallel to make a pregnancy assessment; and
  a support arrangement for supporting the carrier in a desired position relative to the animal, the support arm being mountable on an animal restraint system.

By "fixed" is meant a set of sensors which always have the same geometric position relative to one another and, therefore, form a fixed pattern of contact on the surface of the animal's body, in use. There may be a measure of compliant mounting to ensure a good contact with the animal's body.

The sensors may be arranged in a fixed array. The fixed array of sensors may comprise an array of electrodes arranged in a predetermined relationship with respect to one another. Further, sensors may include at least one audio sensor.

The carrier may mount the sensors flexibly to provide compliant displacement of the sensors in a direction of application of the sensors.

The support arrangement may include a support arm for supporting the carrier. The support arm may be attachable to an animal restraint arrangement such as, for example, an automatic milking system or a fixed-in-place system.

The animal restraint arrangement may be an automatic milking system and the carrier may be responsive to a positioning mechanism of the automatic milking system for positioning the carrier relative to the animal being tested.

Instead, the system may include a dedicated positioning mechanism for positioning the carrier relative to the animal being tested.

The disclosure extends further to an animal restraint system which includes a pregnancy test system, as described above, mounted on it.

The animal restraint system may be an automatic milking system.

In a second aspect, there is provided a method of conducting a pregnancy test on an animal, the method including
- while the animal is being restrained, positioning a carrier carrying a plurality of sensors arranged in a fixed relationship relative to one another in position relative to the animal, the sensors measuring one or more signals representative of the presence of a foetus;
- feeding data from the sensors to signal processing circuitry to process the data to provide an indication of the pregnancy status of the animal being tested; and
- in the signal processing circuitry:
  - minimising artifacts to enable at least one signal of interest to be analysed; and
  - using a plurality of techniques in parallel to analyse to signal of interest to make a pregnancy assessment.

The method may include robotically positioning the carrier relative to the animal.

The method may include restraining the animal in an animal restraint system and using a robotic positioning mechanism of the animal restraint system for positioning the carrier.

The method may include positioning the carrier in the region of an udder of the animal to detect foetal biosignals. In particular, the method may include positioning the carrier on an abdomen of the animal forward of its udder and straddling a sagittal plane of the animal.

Further, the method may include monitoring the animal to obtain biosignals representative of the animal's cardiac activity. In addition, or instead, the method may include monitoring the animal simultaneously to detect foetal biosignals and biosignals representative of the animal's cardiac activity.

BRIEF DESCRIPTION OF DRAWINGS

In the drawings,

FIG. 5 shows a schematic, transverse view of a part of the animal's body indicating where the sensors can be positioned for detecting foetal activity;

FIG. 6 shows a schematic, side view of a part of the animal's body indicating where the sensors can be positioned for detecting maternal cardiac activity;

FIG. 7 shows a schematic, transverse view of a part of the animal's body indicating where the sensors can be positioned for detecting maternal cardiac activity;

DETAILED DESCRIPTION OF EXEMPLARY EMBODIMENTS

Figure 1:
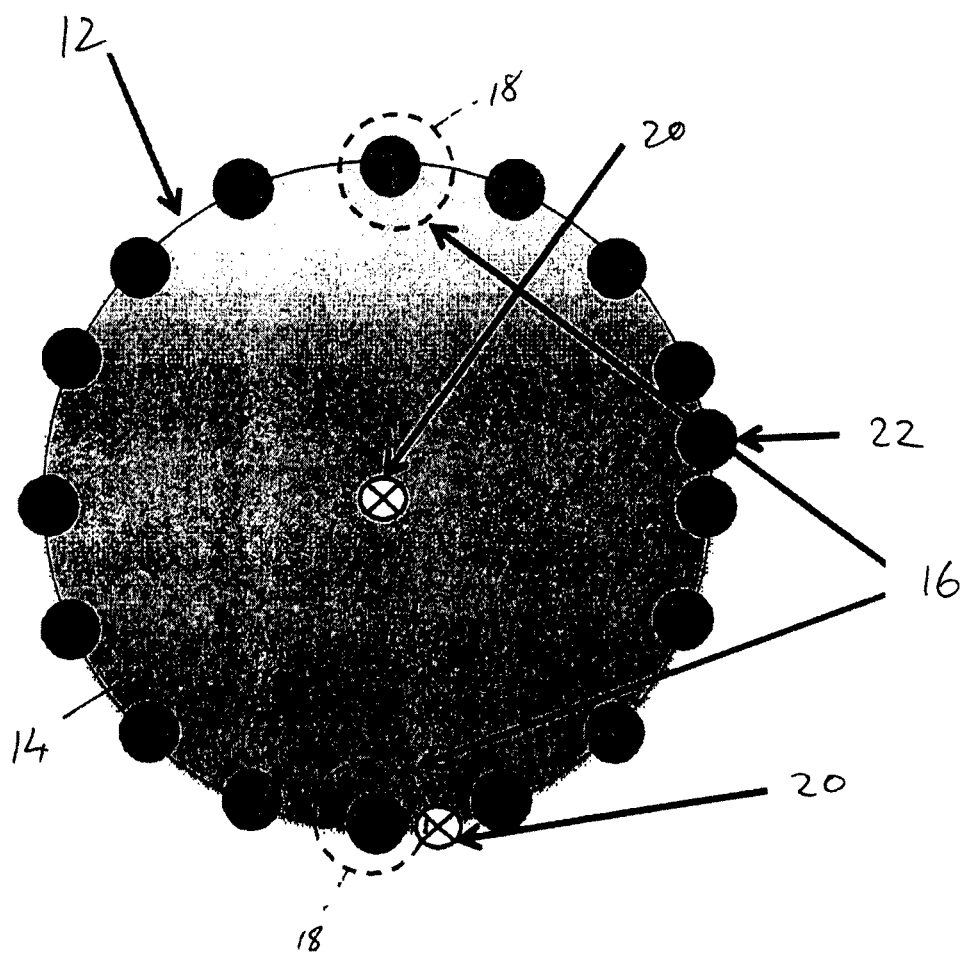
FIG. 1 shows a schematic, front view of an array of sensors mounted on a carrier, the carrier forming part of an embodiment of a pregnancy test system.

In the drawings reference numeral 10 (FIG. 4) generally designates a pregnancy test system. The system 10 is intended particularly for use in monitoring pregnancies in larger agricultural animals, in particular, cows. The system 10 can assess the health of the animal under examination and also detects non-pregnant animals.

The system 10 comprises a sensor array 12 (FIG. 1) mounted on a carrier 14. The sensor array 12 comprises a plurality of electrical sensors in the form of electrodes 16. As indicated by the dotted lines 18 in FIG. 1 of the drawings, the electrodes 16 are arranged in diametrically opposed pairs on the carrier 14. The array 12 also, optionally, includes one or more audio sensors 20. As illustrated, the audio sensors 20 are mounted on an imaginary circle on which the electrodes 16 are arranged or, optionally, in the centre of the carrier 14 or in any other suitable location relative to the carrier 14.

The sensor array 12 further includes an optional ground electrode 22.

The spacing between opposed pairs of electrodes 16 is, generally, less than about 500 mm and, depending on the size of the animal being tested, is greater than about 300 mm. Optimally, the spacing between opposed pairs of electrodes 16, when the system 10 is used for monitoring pregnancy in cows, is no greater than 400 mm.

Figure 2:
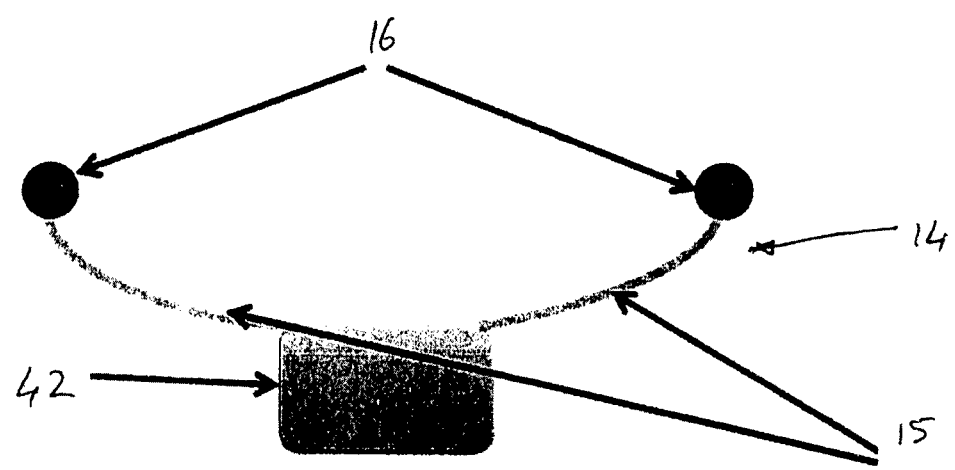
FIG. 2 shows a schematic, sectional side view of an embodiment of the carrier and sensors.

The carrier 14 supports the electrodes 16 of the array 12 in a fixed geometric position with respect to one another. However, the electrodes 16 are resiliently mounted on the carrier 14 so that variations in contours of the animal's body where the sensor array 12 is placed, in use, can be accommodated. In an embodiment, the electrodes 16 are accommodated in the carrier 14 in a compliant manner, for example, by being mounted on spring loaded arms 15 (FIG. 2) within the carrier 14 to accommodate variations in contour and tissue texture. In another embodiment, the carrier 14 is flexible to provide the resilient mounting of the electrodes 16 and the audio sensors 20.

The sensors, be they electrodes 16 or audio sensors 20, are connected to a multi-channel bio-amplifier via a series of connection leads. The bio-amplifier forms part of a signal-processing circuit 42 mounted in the carrier 14. Instead, the signal-processing circuitry could be arranged remotely of the carrier 14 and communicate with the carrier 14 via leads or wirelessly.

Figure 4:
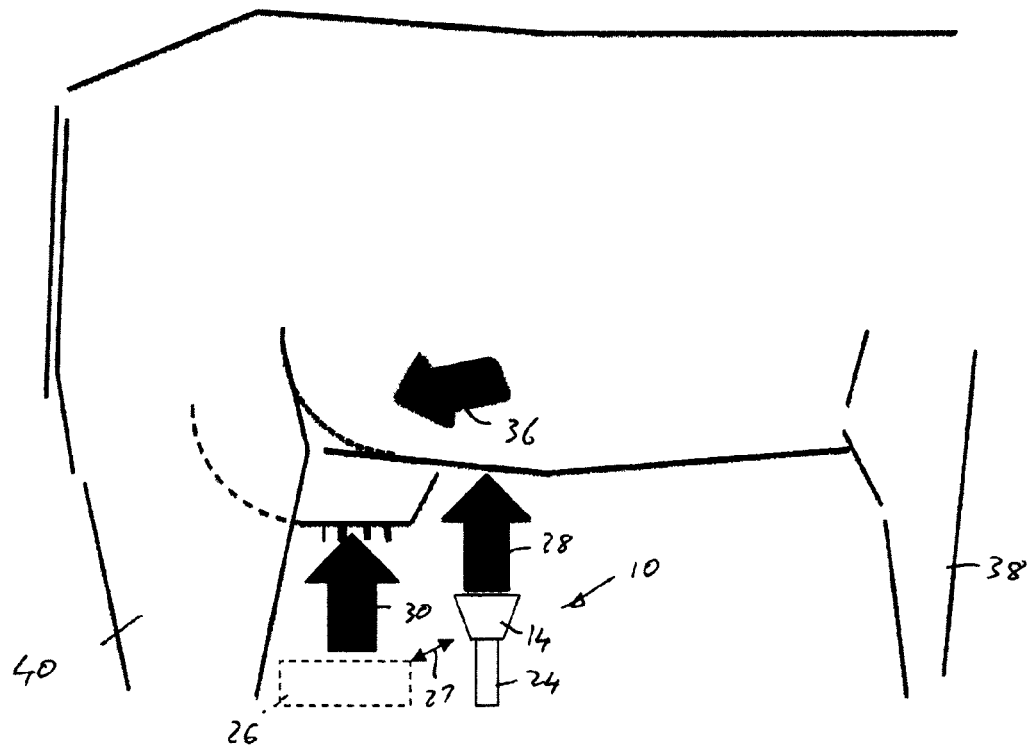
FIG. 4 shows a schematic, side view of a part of the animal's body indicating where the sensors can be positioned for detecting foetal activity.
Figure 8:
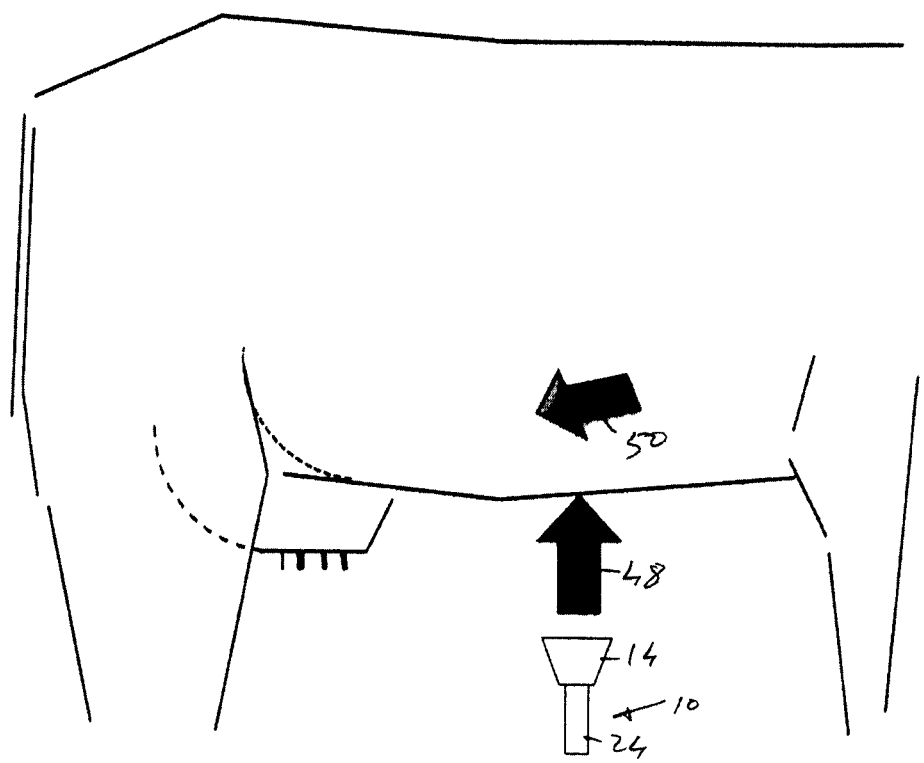
FIG. 8 shows a schematic, side view of a part of the animal's body indicating where the sensors can be positioned for detecting both maternal and foetal cardiac activity.
Figure 9:
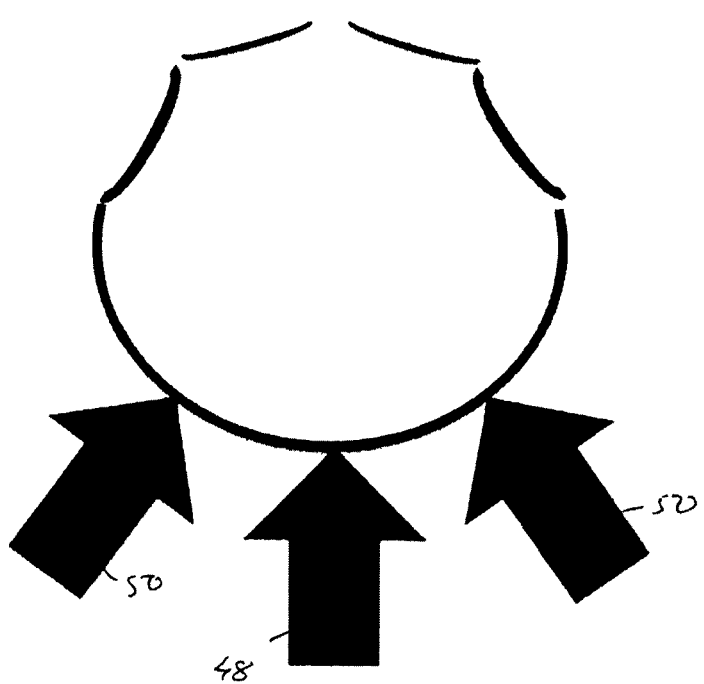
FIG. 9 shows a schematic, transverse view of a part of the animal's body indicating where the sensors can be positioned for detecting both maternal and foetal cardiac activity.

The carrier 14, in turn, is mounted on a support arm 24 (FIG. 4). The arm 24 is, preferably, a robotic arm which is used with an automatic milking system. Instead, the arm 24 could be robotic in its own right or be able to be manipulated manually to position the carrier 14.

Generally, with an automatic milking system, a milking robot applies the milking apparatus (pneumatic cups) to the cow's teats. In order to automate this, a robot is used which has precision three-dimensional positioning and object manipulation capacity. Thus, the automatic milking system includes a positioning mechanism 26 (FIG. 4) by means of which the milking cups are accurately positioned. The positioning mechanism 26 includes a sensor arrangement, typically composed of a three-dimensional laser scanner, possibly augmented with ultrasonic or optical displacement sensors, which enables the automatic milking system to sense the exact position of the cow's udder and teats. The automatic milking system may also, as a regular part of its operation, record the shape and position of each individual cow's udder and make use of this information in cup positioning.

During the actual milking process, the robotic sensor and positioning mechanism 26 are idle. It requires minimal modification to this robotic system to use it to apply the system 10 during the time the positioning mechanism 26 of the automatic milking system is idle. The positioning mechanism 26 is suitably located to guide the pregnancy test system 10 to the correct site on the cow's body as indicated schematically by arrows 27 in FIG. 4 of the drawings.

Figure 3:
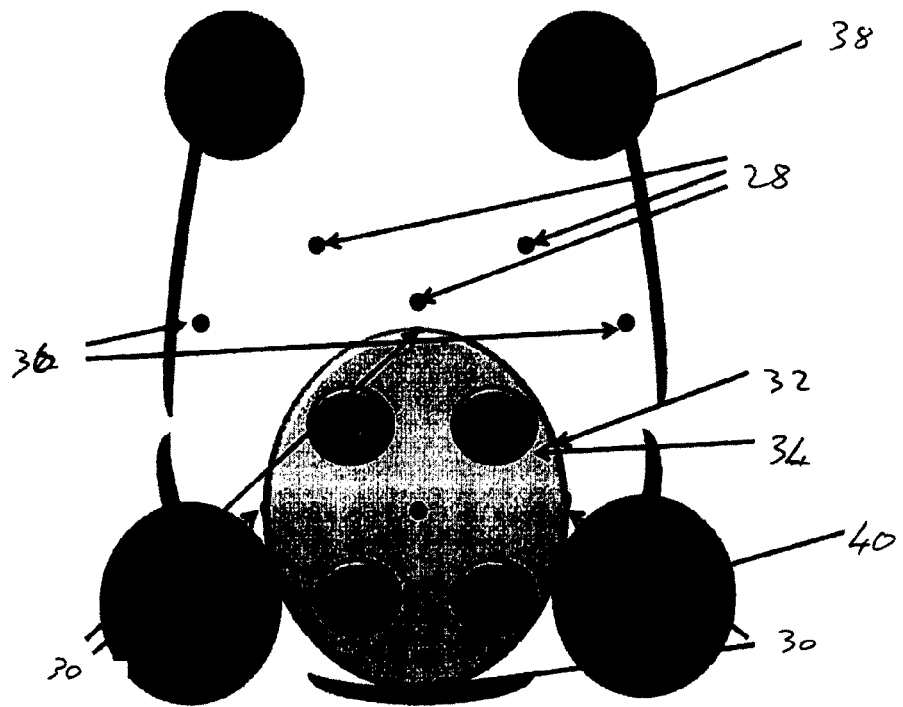
FIG. 3 shows a schematic depiction of an underside of an animal's body indicating positions on the animal's body where the sensors can be placed for detecting foetal activity.

This is particularly advantageous given that a very successful point for the application of the electrode array 12 of the system 10 is the cow's underbelly ahead of the udder as shown by sensor positions 28 in FIG. 3 of the drawings. Other sensor positions are indicated at 30 on the cow's udder 32, on teats 34 of the udder 32 and on lateral milk veins 36 of the cow between an anterior leg 38 and a posterior leg 40 of the cow. Ideally, the locations 28 are positioned about 100 mm-200 mm forward of the forward edge of the udder 32.

For fixed-in-place animal handling systems which do not have robotic sensor positioning mechanisms, the system 10 itself could include such a positioning mechanism 26 for the express purpose of positioning the electrode array 12 or a combination of a mechanical linkage and visual guidance from a trained human operator to apply the pregnancy test system 10 to the cow's body could be used. It will also be appreciated that devices representing intermediate stages of automation may also be viable.

Generally, the system 10 makes use of electrocardiography (ECG) and/or audio outputs to detect pregnancy. In order to do so, a foetal generated biological signal, more particularly, a foetal electrocardiogram (fECG) and/or a foetal phonocardiogram (fPCG) are able to be detected. In addition, maternal generated signals such as a maternal electrocardiogram (mECG) and/or a maternal phonocardiogram (mPCG) may also be detected to assess the health of the animal under test. In addition, in cases of advanced stages of pregnancy, foetal movements can be detected as well to assess the stress level of the foetus.

As indicated above, there are several appropriate locations on the cow's body where the foetal signals can be detected and it has been found that a very suitable location for detecting a fECG is that shown by sensor markings 28 in FIG. 3 of the drawings, i.e approximately 100 mm-200 mm in front of the udder 32 straddling the sagittal plane of the animal.

It is to be noted that it is not necessary always to measure both an electrical signal and an audio signal and it is possible to use only one kind of sensor. The minimum requirements for the system are, in the case an electrical system, one channel equipped with two electrodes. The minimum requirements for an audio system are one channel equipped with a suitable audio sensor. Thus, the minimum requirements for a combined system is one channel equipped with two electrodes and one channel equipped with one suitable audio sensor.

In addition to detecting pregnancy, the health of the cow can also be detected. While the position shown by arrows 28 in FIG. 3 of the drawings may be useful for this purpose, it has been found that two further positions as indicated by arrows 44 and 46 (FIGS. 6 and 7) are preferred for monitoring the cardiac health of the mother. As indicated in FIG. 7 of the drawings, the position 46 can be on either side of the animal.

Still further, the system 10 can be used to assess the maternal health or the health of any post-natal animal by applying the system 10 to the chest wall in the positions indicated in FIGS. 6 and 7 of the drawings. This will allow the recording of an ECG signal that can be used to assess animal cardiac health in a similar manner to that in which human cardiac health is assessed by a cardiologist using an ECG.

In FIGS. 8 to 11 of the drawings, a further embodiment of the system 10 and method are illustrated.

In this embodiment, the carrier 14 is positioned approximately midway between the positions shown in FIGS. 4 and 5 of the drawings and the positions shown in FIGS. 6 and 7 of the drawings. Thus, the carrier 14 is able to be positioned on the sagittal plane of the animal as indicated by arrow 48 or on either side of the sagittal plane as indicated by arrows 50. In this position, the maternal heartbeat and, if the animal is pregnant, the foetal heartbeat are able to be detected simultaneously.

Figure 10:
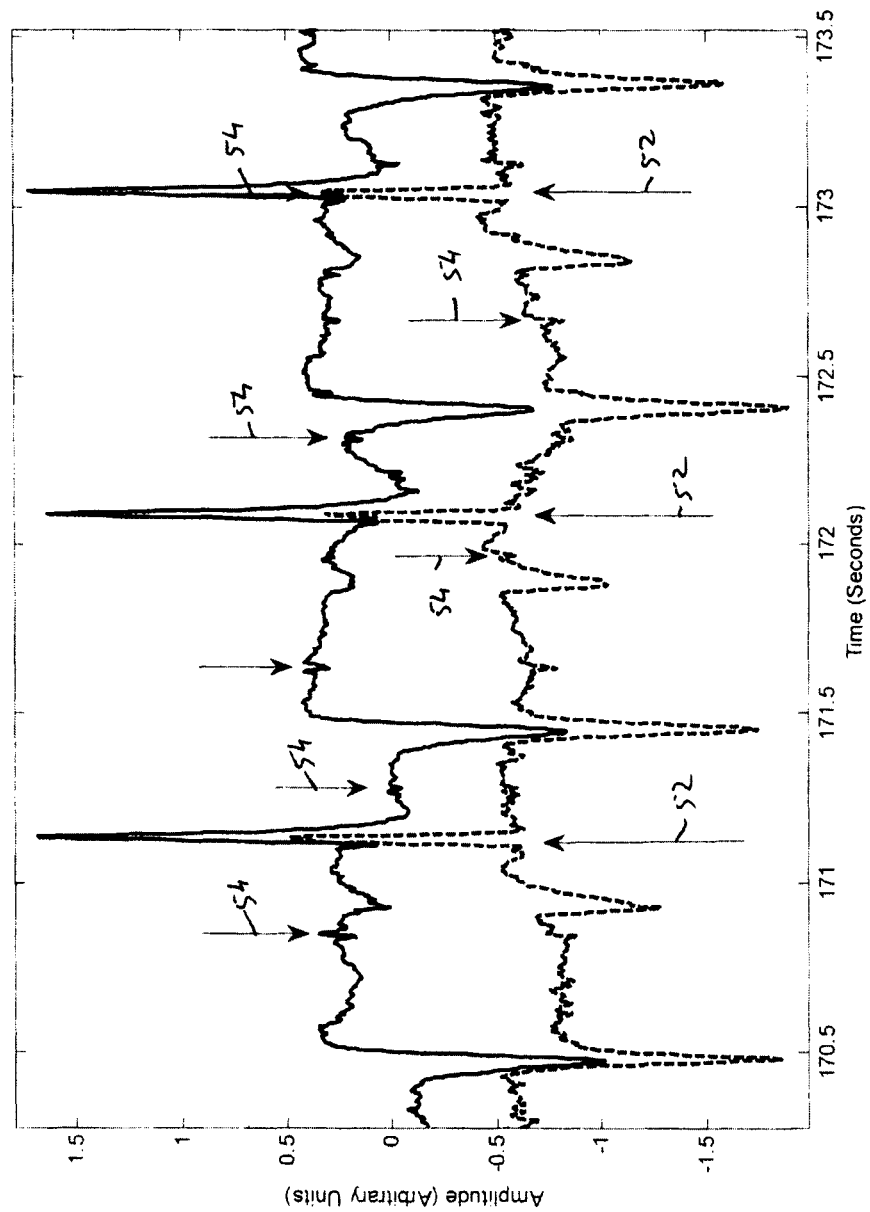
FIG. 10 shows a waveform representative of maternal and foetal cardiac activity.
Figure 11:
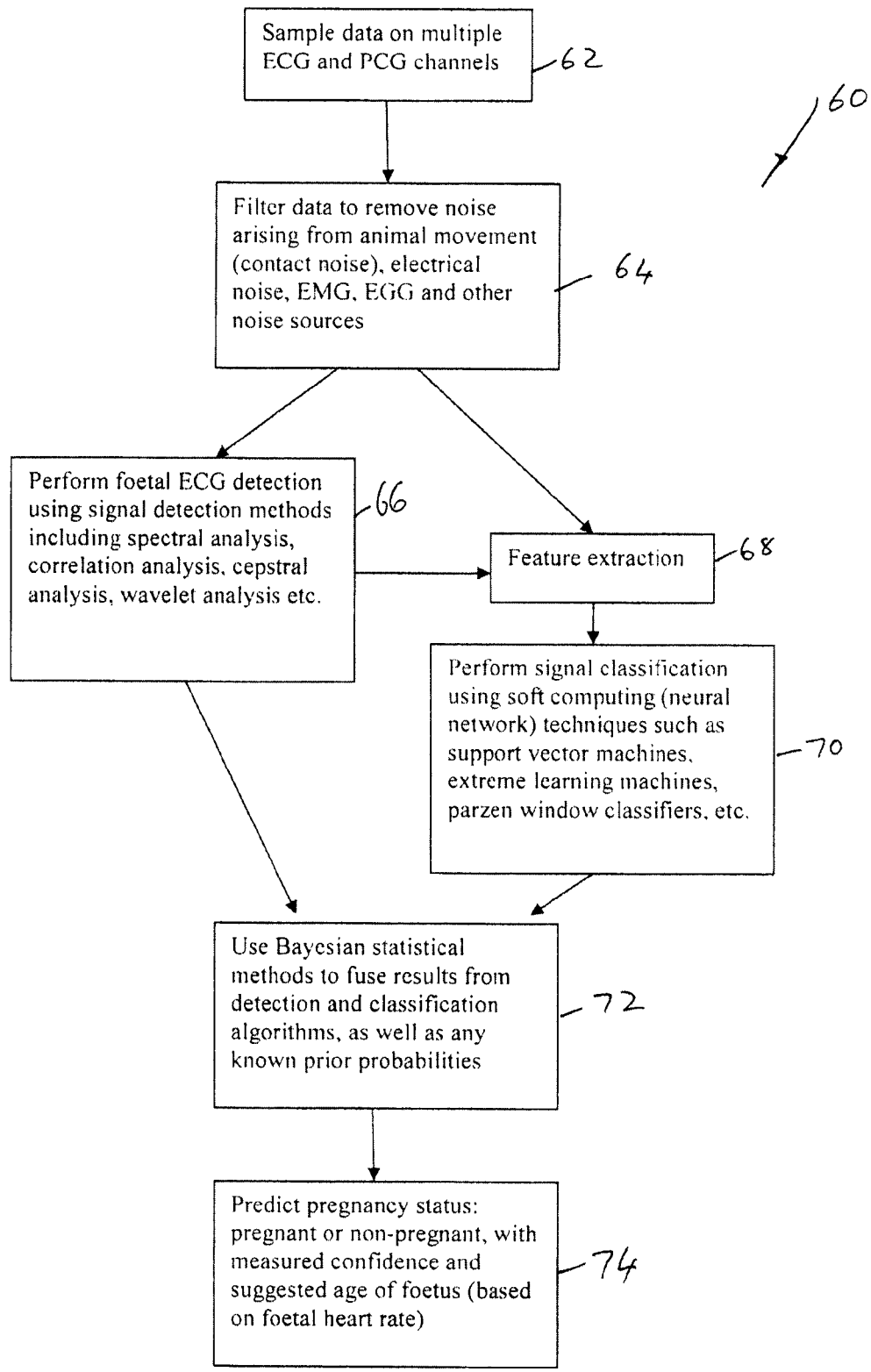
FIG. 11 shows a flow chart of steps of an embodiment of a method of conducting a pregnancy test.

An excerpt of data representing combined recording of maternal and foetal ECGs is depicted in FIG. 10 of the drawings for two ECG leads from the sensor array 12. Maternal QRS complexes of the ECG are highlighted by arrows 52 pointing upwardly while foetal QRS complexes are highlighted by arrows 54 pointing downwardly. As is to be expected, in some cases foetal beats are more evident on one of the sensors 16 and vice versa.

Referring now to FIG. 12 of the drawings, a flow chart of an embodiment of a method of conducting a pregnancy test is shown and is designated generally by the reference numeral 60. The method is described below with reference to the flow chart 60.

Once the carrier 14 has been positioned relative to the animal to be assessed, the sensors 16 detect signals. The signals are ECG signals detected by the electrodes 18 and audio signals measured by the audio sensors 20. Hence, the signal processing circuit 42 takes as its input the biological signals from the potentially pregnant animal which may include mECG and fECG signals and mPCG and fECG signals as shown at step 62. As initial steps (not shown), the detected signals are amplified and filtered electronically before being sampled and digitized by the signal processing circuit 42. The remainder of the process takes place in software within the signal processing circuit 42.

As shown at step 64, the digitized data are further filtered to remove as much noise as is possible without compromising the useful signal in the sampled data. This filtering includes bandpass and nonlinear filtering to remove electrical noise arising from conventional electronic noise sources as well as that noise which may arise from poor physical or electrical contact between the sensors 16 and the animal. There are also biosignals which emanate from the animal, such as electromyographic (EMG) signals and electrogastrographic (EGG) signals, which detract from the signal qualities required for pregnancy detection and which are treated as noise and removed as far as possible.

The data are then processed in order to make a diagnosis of pregnancy. There are many possible approaches for this, and most can be used in parallel. For example, as shown at step 66, techniques of signal detection are used. These techniques include using a matched filter to enhance the visibility of heartbeat events in the signal; the use of wavelet or spectral analysis to identify and enhance the heart beat signals through their known consistency of frequency components; the use of correlation methods such as auto-correlation and cross-correlation to enhance and detect the signal through the known periodicity of the signal; or the use of cepstral analysis to do the same. These techniques fundamentally work by identifying the occurrence of heartbeat events in the biosignals and discriminating them to be foetal or maternal heartbeats by means of heart rate, coherence, location, or other distinguishing features. The detection of foetal heartbeat suggests the presence of a foetus and hence pregnancy, while the absence of foetal heart beat suggests non-pregnancy.

In an alternate step as shown at 68, features from the sampled and noise-removed biosignals which are thought to embody evidence of foetal presence are extracted. These features include some of the coefficients of the signals derived in the signal detection methods of step 66, such as the coefficients of the wavelet transform of the ECG signal.

The extracted features are then fed into a classification algorithm as shown at step 70. Typical examples of classification algorithms which are able to be used include support vector machines, extreme learning machines, parzen window classifiers, or the like. These classification algorithms are trained on large bodies of data from animals which are known to be pregnant or non-pregnant and are able to "learn" the difference between the features extracted from these two classes and, hence, when presented with a new set of data they can classify the data into one or other class.

All of the methods used in step 66 and/or step 70 have the facility of returning a confidence value in their diagnosis, which itself is useful information. In making a final decision, the signal processing circuit 42 takes into account the diagnosis, and the confidence of diagnosis, from several such detection and/or classification schemes. The signal processing circuit uses methods of Bayesian statistics to combine the outputs from step 66 and/or step 70 with so-called prior information on, for example, the historical accuracy of each method, or the expected proportion of animals which are pregnant, and makes an appropriately weighted decision as shown at steps 72 and 74. In addition to making a diagnosis of pregnancy or non-pregnancy, the signal processing circuit 42, in the case of a pregnant outcome, also is able to make an estimate of foetal age, for example, by comparing the apparent foetal heart rate against known age-to-heart rate distributions.

It is a particular advantage of the described embodiment that the system 10 does not require any skilled operator to use it. When integrated into an automated milking system, it is also completely automated. In addition, stress to the animal is minimised since the animals have been trained to self-position themselves in the automated milking system so are familiar with the machinery surrounding them and use of the system 10 on the animals will not cause additional stress to the animals.

Also, once again with use of the system 10 with an automated milking system, the need for separate positioning systems is obviated.

It will be appreciated by persons skilled in the art that numerous variations and/or modifications may be made to the disclosure as shown in the specific embodiments without departing from the scope of the disclosure as broadly described.

The present embodiments are, therefore, to be considered in all respects as illustrative and not restrictive.

The invention claimed is:

1. A pregnancy test system which includes
   a carrier carrying a plurality of sensors arranged in a fixed relationship relative to one another;
   a signal processing circuit for processing data sensed by the sensors and for outputting a data signal representative of the pregnancy status of an animal being examined, the signal processing circuit being operative to minimise artifacts to enable at least one signal of interest to be analysed in the signal processing circuitry using a plurality of techniques in parallel to make a pregnancy assessment; and
   a support arrangement for supporting the carrier in a desired position relative to the animal, the support arrangement being mountable on an animal restraint system, the animal restraint system being an automatic milking system and the carrier being responsive to a positioning mechanism of the automatic milking system for positioning the carrier relative to the animal being tested.

2. The system of claim 1 in which the sensors are arranged in a fixed array.

3. The system of claim 2 in which the fixed array of sensors comprises an array of electrodes arranged in a predetermined relationship with respect to one another.

4. The system of claim 1 in which the sensors include at least one audio sensor.

5. The system of claim 1 in which the carrier mounts the sensors flexibly to provide compliant displacement of the sensors in a direction of application of the sensors.

6. The system of claim 1 in which the support arrangement includes a support arm for supporting the carrier.

7. The system of claim 6 in which the support arm is attachable to the animal restraint arrangement.

8. The system of claim 1 which includes a dedicated positioning mechanism for positioning the carrier relative to the animal being tested.

9. An animal restraint system which includes a pregnancy test system, as claimed claim 1, mounted on it.

10. A method of conducting a pregnancy test on an animal, the method including while the animal is being restrained in an automatic milking machine, using a robotic positioning mechanism of the automatic milking system to position a carrier carrying a plurality of sensors arranged in a fixed relationship relative to one another in position relative to the animal, the sensors measuring one or more signals representative of the presence of a foetus;
    feeding data from the sensors to signal processing circuitry to process the data to provide an indication of the pregnancy status of the animal being tested; and
    in the signal processing circuitry:
    minimising artifacts to enable at least one signal of interest to be analysed; and
    using a plurality of techniques in parallel to analyse to signal of interest to make a pregnancy assessment.

11. The method of claim 10 which includes robotically positioning the carrier relative to the animal.

12. The method of claim 10 which includes positioning the carrier in the region of an udder of the animal to detect foetal biosignals.

13. The method of claim 12 which includes positioning the carrier on an abdomen of the animal forward of its udder and straddling a sagittal plane of the animal.

14. The method of claim 12 which includes monitoring the animal to obtain biosignals representative of the animal's cardiac activity.

15. The method of claim 14 which includes monitoring the animal simultaneously to detect foetal biosignals and biosignals representative of the animal's cardiac activity.

16. A pregnancy test system which includes
    a carrier carrying a plurality of sensors arranged in a fixed relationship relative to one another;
    a signal processing circuit for processing data sensed by the sensors and for outputting a data signal representative of the pregnancy status of an animal being examined, the signal processing circuit being operative to minimise artifacts to enable at least one signal of interest to be analysed in the signal processing circuitry using a plurality of techniques in parallel to make a pregnancy assessment; and a support arrangement for supporting the carrier in a desired position on an abdomen of the animal forward of an udder of the animal and straddling a sagittal plane of the animal, the support arrangement being mountable on an animal restraint system.

17. A method of conducting a pregnancy test on an animal, the method including while the animal is being restrained, positioning a carrier on an abdomen of the animal forward of an udder of the animal and straddling a sagittal plane of the animal, the carrier carrying a plurality of sensors arranged in a fixed relationship relative to one another and the sensors measuring one or more signals representative of the presence of a foetus;

feeding data from the sensors to signal processing circuitry to process the data to provide an indication of the pregnancy status of the animal being tested; and in the signal processing circuitry:

minimising artifacts to enable at least one signal of interest to be analysed; and using a plurality of techniques in parallel to analyse to signal of interest to make a pregnancy assessment.

* * * * *